(12) United States Patent
Neupert et al.

(10) Patent No.: US 10,905,536 B2
(45) Date of Patent: Feb. 2, 2021

(54) APPARATUS FOR TREATMENT OF POULTRY

(71) Applicant: Andrew Neupert, Melrose, MN (US)

(72) Inventors: Andrew Neupert, Melrose, MN (US); Gilbert H. Warriner, Willmar, MN (US)

( * ) Notice: Subject to any disclaimer, the term of this patent is extended or adjusted under 35 U.S.C. 154(b) by 596 days.

(21) Appl. No.: 15/456,825

(22) Filed: Mar. 13, 2017

(65) Prior Publication Data

US 2018/0256303 A1 Sep. 13, 2018

(51) Int. Cl.
| | |
|---|---|
| *A61D 1/02* | (2006.01) |
| *B05B 7/24* | (2006.01) |
| *A01K 45/00* | (2006.01) |
| *B05B 7/00* | (2006.01) |
| *B05B 15/62* | (2018.01) |

(52) U.S. Cl.
CPC .............. *A61D 1/025* (2013.01); *A01K 45/00* (2013.01); *B05B 7/0093* (2013.01); *B05B 7/2486* (2013.01); *B05B 7/2489* (2013.01); *B05B 7/2491* (2013.01); *B05B 15/62* (2018.02)

(58) Field of Classification Search
CPC ...... A01K 45/00; A01K 13/003; A61D 1/025; A61D 7/00; B05B 7/2491; B05B 7/0093; B05B 7/2486; B05B 7/2489
See application file for complete search history.

(56) References Cited

U.S. PATENT DOCUMENTS

| | | | | |
|---|---|---|---|---|
| 1,767,560 | A | * | 6/1930 | Snyder ................ A01K 13/003 119/667 |
| 2,532,251 | A | | 11/1950 | Whitmire et al. |
| 3,163,149 | A | * | 12/1964 | Ivey ...................... A01K 1/031 119/479 |
| 3,490,695 | A | * | 1/1970 | Rittenhouse ........ A01M 7/0014 239/77 |
| 3,521,817 | A | | 7/1970 | Curtis et al. |
| 3,699,928 | A | * | 10/1972 | Cowan ................ A01K 13/003 119/667 |
| 4,121,738 | A | * | 10/1978 | Virag .................. B01F 15/0237 222/134 |

(Continued)

FOREIGN PATENT DOCUMENTS

| | | | | |
|---|---|---|---|---|
| DE | 4122594 | A1 * | 11/1992 | ............ B05B 7/067 |
| EP | 1464406 | A2 * | 10/2004 | ........... B05B 7/2486 |
| WO | WO-2015195044 | A1 * | 12/2015 | ........... B05B 7/2429 |

*Primary Examiner* — Magdalena Topolski
(74) *Attorney, Agent, or Firm* — Cardle Patent Law CHTD

(57) ABSTRACT

A poultry treatment apparatus disclosed herein may include a tank forming a reservoir at ambient pressure and containing liquid. A pump may be in fluid communication with the tank, and the pump may be in fluid communication with a liquid intake of a first nozzle, and in fluid communication with a liquid intake of a second nozzle to supply liquid under pressure from the tank to the liquid intake of the first nozzle and to the liquid intake of the second nozzle. A compressor may be in fluid communication with an air intake of the first nozzle and with an air intake of the second nozzle to supply compressed air to the air intake of the first nozzle and to the air intake of the second nozzle. In various aspects, the combination of compressed air and liquid under pressure deliver spray from the first nozzle and deliver spray from the second nozzle at about the same flow rate of liquid with droplets of similar size.

11 Claims, 8 Drawing Sheets

(56) References Cited

U.S. PATENT DOCUMENTS

| | | | |
|---|---|---|---|
| 4,316,464 A | 2/1982 | Peterson | |
| 4,449,968 A * | 5/1984 | Peterson | A61D 1/025 |
| | | | 604/24 |
| 4,643,354 A | 2/1987 | Stowe | |
| 4,863,443 A * | 9/1989 | Hornung | A61D 1/025 |
| | | | 604/500 |
| 4,947,802 A | 8/1990 | Fisinin et al. | |
| 4,991,776 A * | 2/1991 | Smith | B05B 7/0081 |
| | | | 137/895 |
| 5,063,880 A * | 11/1991 | Bouthillier | A01K 13/001 |
| | | | 119/667 |
| 5,109,797 A * | 5/1992 | Briant | A61D 7/04 |
| | | | 119/420 |
| 5,460,192 A * | 10/1995 | McClain | A01K 13/001 |
| | | | 119/665 |
| 5,468,227 A * | 11/1995 | Haskell | A61D 1/025 |
| | | | 119/713 |
| 5,830,511 A * | 11/1998 | Mullerat | A01N 59/00 |
| | | | 424/661 |
| 5,884,583 A * | 3/1999 | Johnston, Jr. | A01K 7/02 |
| | | | 119/72 |
| 6,606,966 B1 | 8/2003 | Teachey et al. | |
| 6,910,446 B2 | 6/2005 | Johnston Jr. | |
| 6,951,073 B2 | 10/2005 | Moore et al. | |
| 7,073,734 B2 | 7/2006 | Dorendorf et al. | |
| 7,380,730 B2 | 6/2008 | Bertoni | |
| 8,087,386 B2 | 1/2012 | Purswell et al. | |
| 8,438,996 B2 | 5/2013 | Greeson | |
| 8,794,185 B2 | 8/2014 | Lee | |
| 8,881,998 B1 * | 11/2014 | Sinkfield | A61F 7/0053 |
| | | | 119/665 |
| 2001/0010208 A1 | 8/2001 | Greeson | |
| 2002/0104485 A1 | 8/2002 | Lewis et al. | |
| 2005/0217589 A1 | 10/2005 | Daniel et al. | |
| 2006/0275555 A1 * | 12/2006 | Colizza | B05B 16/40 |
| | | | 427/458 |
| 2007/0252020 A1 | 11/2007 | Smeraldi | |
| 2009/0025794 A1 | 1/2009 | Dorendorf et al. | |
| 2010/0186680 A1 | 7/2010 | Matsumara et al. | |
| 2011/0217322 A1 * | 9/2011 | Purswell | A61D 1/025 |
| | | | 424/184.1 |
| 2012/0193458 A1 | 8/2012 | Wheeler et al. | |
| 2015/0053788 A1 | 2/2015 | Park et al. | |
| 2015/0128873 A1 | 5/2015 | Prescott et al. | |
| 2015/0144071 A1 | 5/2015 | Samson et al. | |
| 2015/0148771 A1 | 5/2015 | Samson et al. | |
| 2015/0230428 A1 * | 8/2015 | Fussell, Jr. | A01K 13/001 |
| | | | 119/667 |
| 2016/0151796 A1 | 6/2016 | Johnson | |
| 2016/0158465 A1 | 6/2016 | Coats et al. | |
| 2016/0338815 A1 * | 11/2016 | Nguyen | A61M 11/02 |

* cited by examiner

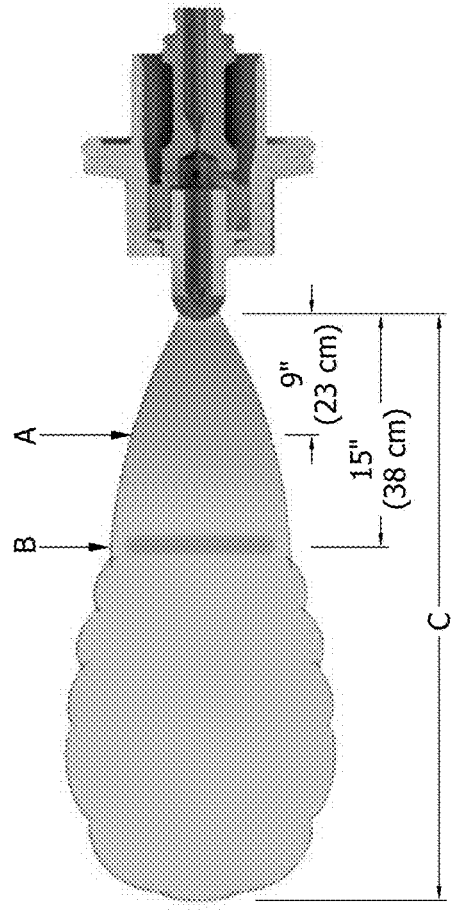

For these QuickMist flat spray set-ups, "A" and "B" are the pattern widths at distances from the nozzle.

The total distance of spray projection from the nozzle to the maximum dispersal point is represented by "C".

Liquid is supplied to this spray set-up under pressure.

Liquid and compressed air or gas are mixed internally to product a completely atomized spray.

| Spray Set-up No. | Spray Set-up Consists of Fluid & Air Cap Combo | Liquid Capacity (gallons per hour)* and Air Capacity (standard cubic feet per minute)* | | | | | | | | | | | | | | | | | | Spray Dimensions | | |
|---|---|---|---|---|---|---|---|---|---|---|---|---|---|---|---|---|---|---|---|---|---|---|
| | | Liquid Pressure | | | | | | | | | | | | | | | | | | | | |
| | | 20 psi | | | 30 psi | | | 40 psi | | | 50 psi | | | 60 psi | | | 70 psi | | | A (in.) | B (in.) | C (ft.) |
| | | Air Press. | gph | scfm | Air Press. | gph | scfm | Air Press. | gph | scfm | Air Press. | gph | scfm | Air Press. | gph | scfm | Air Press. | gph | scfm | | | |
| SUQF-130 | Fluid Cap PFQ20 + Air Cap PAWF28 | 20 | 1.5 | 1.3 | 20 | 2.9 | 1.1 | 20 | 3.9 | 1.1 | - | - | - | - | - | - | - | - | - | 5-10 | 7-14 | 10-21 |
| | | - | - | - | 30 | 1.7 | 1.7 | 30 | 3.0 | 1.5 | 30 | 4.0 | 1.4 | 30 | 4.7 | 1.4 | - | - | - | | | |
| | | - | - | - | - | - | - | 40 | 1.9 | 2.1 | 40 | 3.1 | 1.9 | 40 | 4.1 | 1.8 | 40 | 4.9 | 1.7 | | | |
| | | - | - | - | - | - | - | - | - | - | 50 | 2.0 | 2.4 | 50 | 3.2 | 2.3 | 50 | 4.1 | 2.2 | | | |
| | | - | - | - | - | - | - | - | - | - | - | - | - | 60 | 2.2 | 2.8 | 60 | 3.3 | 2.6 | | | |
| | | - | - | - | - | - | - | - | - | - | - | - | - | - | - | - | 70 | 2.4 | 3.2 | | | |
| SUQFN-130 | Fluid Cap PFQ30 + Air Cap PAQF28 | 20 | 2.7 | 1.1 | - | - | - | - | - | - | - | - | - | - | - | - | - | - | - | 8-12 | 11-19 | 14-27 |
| | | - | - | - | 30 | 3.1 | 1.5 | 30 | 5.9 | 1.2 | - | - | - | - | - | - | - | - | - | | | |
| | | - | - | - | - | - | - | 40 | 3.4 | 1.8 | 40 | 6.0 | 1.5 | - | - | - | - | - | - | | | |
| | | - | - | - | - | - | - | - | - | - | 50 | 3.7 | 2.2 | 50 | 6.1 | 1.9 | 50 | 8.1 | 1.7 | | | |
| | | - | - | - | - | - | - | - | - | - | - | - | - | 60 | 4.0 | 2.5 | 60 | 6.2 | 2.2 | | | |
| | | - | - | - | - | - | - | - | - | - | - | - | - | - | - | - | 70 | 4.2 | 2.8 | | | |

*At the stated pressure in psi.

_APPARATUS FOR TREATMENT OF POULTRY_

BACKGROUND OF THE INVENTION

Field

This disclosure relates to apparatus and related methods for poultry treatment, and, more specifically to apparatus that deliver vaccine as a spray simultaneously to poultry disposed on multiple tiers.

Background

Poultry are susceptible to various diseases particularly when congregated in large numbers in close quarters. In order to prevent disease, poultry farmers deliver vaccine to poultry by spraying a mist of liquid droplets containing vaccine onto the poultry. The droplets in the mist may land upon the poultry, and the poultry may then ingest the droplets while grooming thus delivering the vaccine to the poultry. Poultry may inhale the droplets, or the poultry may ingest feed or other material that includes the droplets.

Poultry, as used herein, includes, for example, chickens, turkeys, guinea hens, Cornish hens, ducks, geese, and other domesticated birds raised either for meat or for eggs.

Poultry may be arranged in tiers in a poultry barn with the tiers stacked one above the other with narrow pathways along the tiers. In such settings, delivery of vaccine by spray has been performed using devices that require the user to direct the spray about each tier while traversing the narrow pathway. This is time inefficient and may result in unequal distribution of vaccine among a flock. While other devices may allow for spraying multiple tiers, these devices are complex, tend to clog, and may also deliver the vaccine unequally.

Accordingly, there is a need for improved apparatus as well as related methods that deliver vaccine to flocks of poultry that may be arranged on multiple tiers.

BRIEF SUMMARY OF THE INVENTION

These and other needs and disadvantages may be overcome by the apparatus and related methods of use disclosed herein. Additional improvements and advantages may be recognized by those of ordinary skill in the art upon study of the present disclosure.

A poultry treatment apparatus is disclosed herein. In various aspects, the poultry treatment apparatus may include a tank forming a reservoir at ambient pressure and containing liquid. A pump may be in fluid communication with the tank, and the pump may be in fluid communication with a liquid intake of a first nozzle, and in fluid communication with a liquid intake of a second nozzle to supply liquid under pressure from the tank to the liquid intake of the first nozzle and to the liquid intake of the second nozzle. A compressor may be in fluid communication with an air intake of the first nozzle and with an air intake of the second nozzle to supply compressed air to the air intake of the first nozzle and to the air intake of the second nozzle. The air pressure $p_g$ is independent of the liquid pressure $p_h$ in various aspects. In various aspects, the combination of compressed air and liquid under pressure deliver spray from the first nozzle and deliver spray from the second nozzle, and the first nozzle and the second nozzle may deliver about the same flow rate of liquid and may have droplets of similar size. The first nozzle is secured to a boom at a first elevation to deliver spray into a first tier, and a second nozzle secured to the boom at a second elevation to deliver spray into a second tier, the second tier being at a different elevation than the first tier, in various aspects. The tank, the compressor, the pump, and the boom are attached to a cart traversable to deliver spray simultaneously to poultry contained on the first tier and poultry contained on the second tier, in various aspects.

Related methods of poultry treatment are also disclosed herein. In various aspects, the methods of poultry treatment may include the steps of traversing a cart with a boom attached thereto, the boom having a first nozzle at a first elevation and a second nozzle at a second elevation along a first tier and a second tier containing poultry, and delivering spray simultaneously to poultry contained on the first tier at a first elevation through the first nozzle and poultry contained on the second tier at a second elevation through the second nozzle by delivering liquid to the first nozzle and the second nozzle using a pump disposed about the cart and delivering air to the first nozzle and the second nozzle using a compressor disposed about the cart. The liquid pressure at the nozzle is greater than the gas pressure at the nozzle and the liquid comprises a vaccine, in various aspects.

This summary is presented to provide a basic understanding of some aspects of the apparatus and methods disclosed herein as a prelude to the detailed description that follows below. Accordingly, this summary is not intended to identify key elements of the apparatus and methods disclosed herein or to delineate the scope thereof.

Figure 1A:
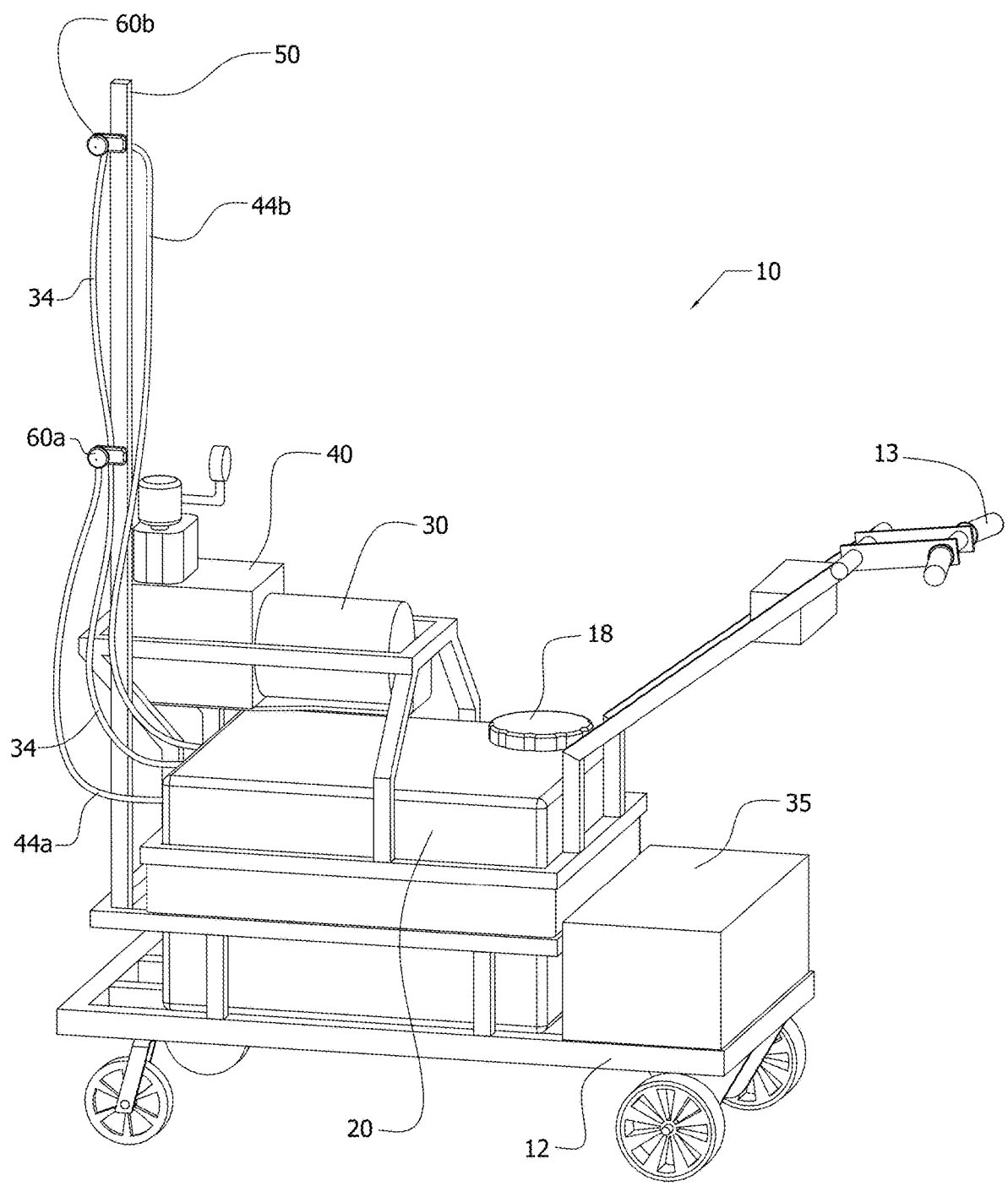
FIG. 1A illustrates by perspective view an exemplary implementation of a poultry treatment apparatus according to the present inventions.

The Figures are exemplary only, and the implementations illustrated therein are selected to facilitate explanation. The number, position, relationship and dimensions of the elements shown in the Figures to form the various implementations described herein, as well as dimensions and dimensional proportions to conform to specific force, weight, strength, flow and similar requirements are explained herein or are understandable to a person of ordinary skill in the art upon study of this disclosure. Where used in the various Figures, the same numerals designate the same or similar elements. Furthermore, when the terms "top," "bottom," "right," "left," "forward," "rear," "first," "second," "inside," "outside," and similar terms are used, the terms should be understood in reference to the orientation of the implementations shown in the drawings and are utilized to facilitate description thereof. Use herein of relative terms such as generally, about, approximately, essentially, may be indicative of engineering, manufacturing, or scientific tolerances such as ±0.1%, ±1%, ±2.5%, ±5%, or other such tolerances, as would be recognized by those of ordinary skill in the art upon study of this disclosure.

DETAILED DESCRIPTION OF THE INVENTION

Figure 1B:
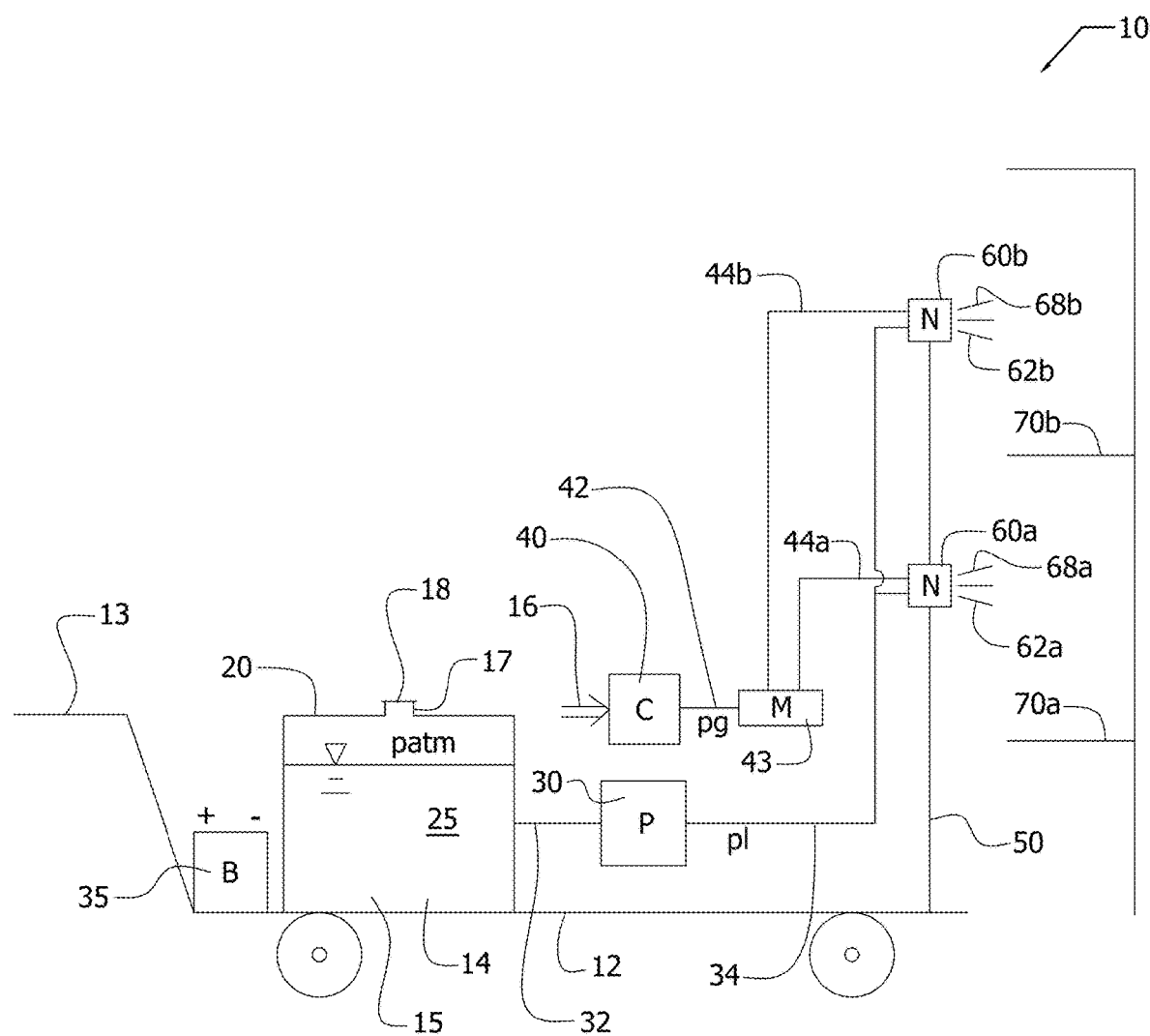
FIG. 1B illustrates by schematic diagram the exemplary implementation of a poultry treatment apparatus of FIG. 1A.
Figure 2:
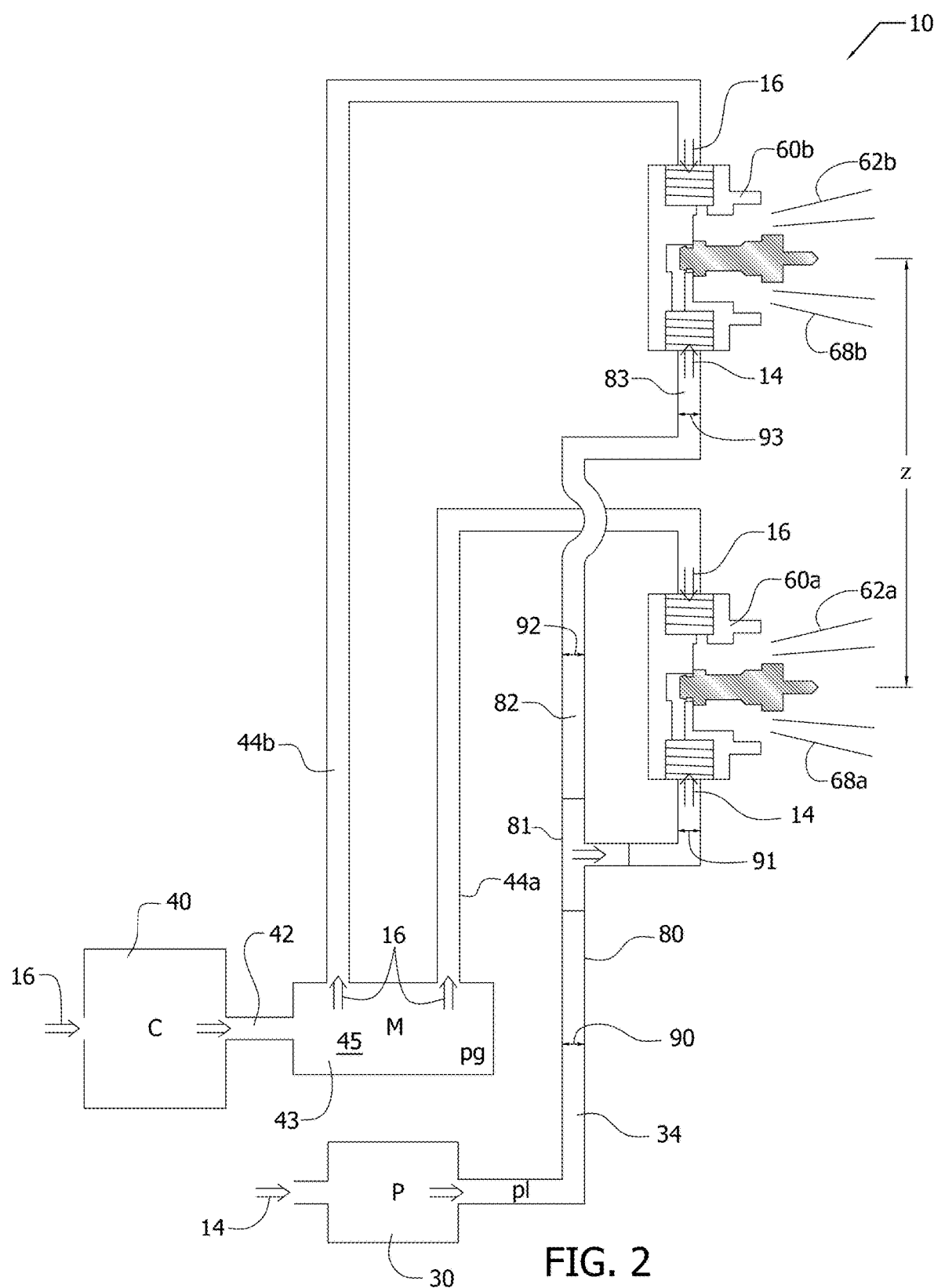
FIG. 2 illustrates by schematic diagram portions of the exemplary implementation of a poultry treatment apparatus of FIG. 1A.
Figure 3:
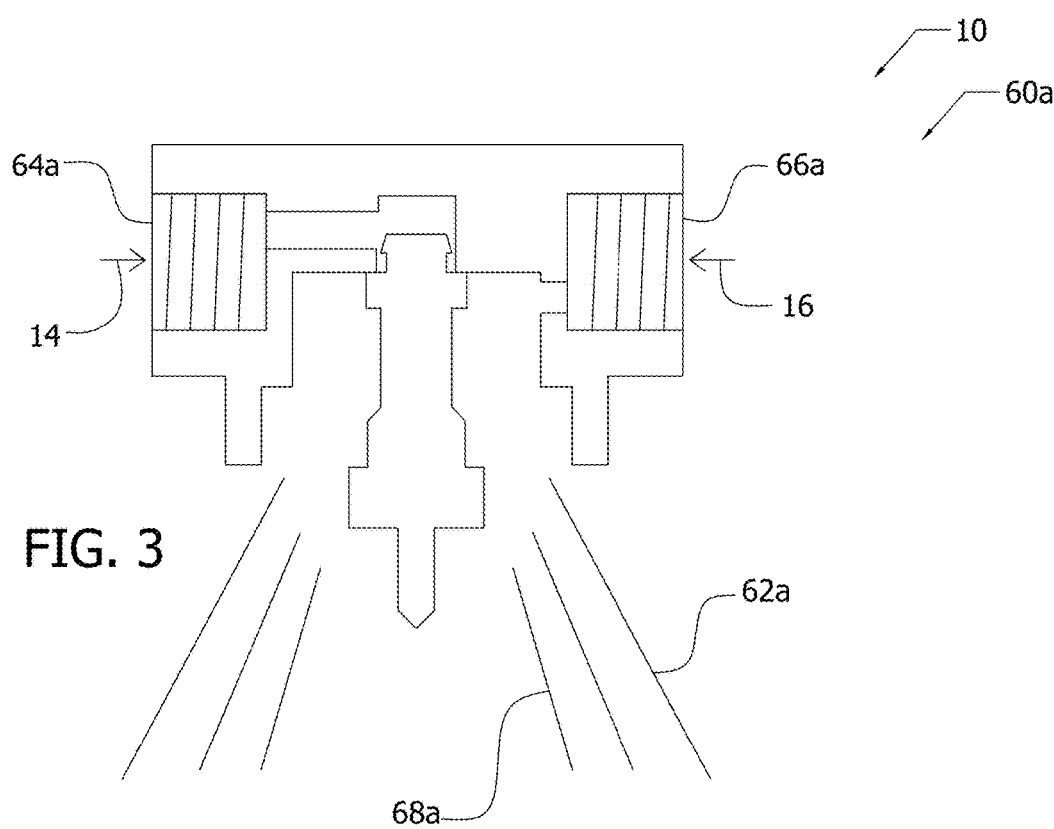
FIG. 3 illustrates by cut-away view portions of the exemplary implementation of a poultry treatment apparatus of FIG. 1A including an exemplary Quickmist® ¼ QMJ nozzle as may be included in various implementation of a poultry treatment apparatus according to the present inventions.
Figures 4A, 4B, 4C:
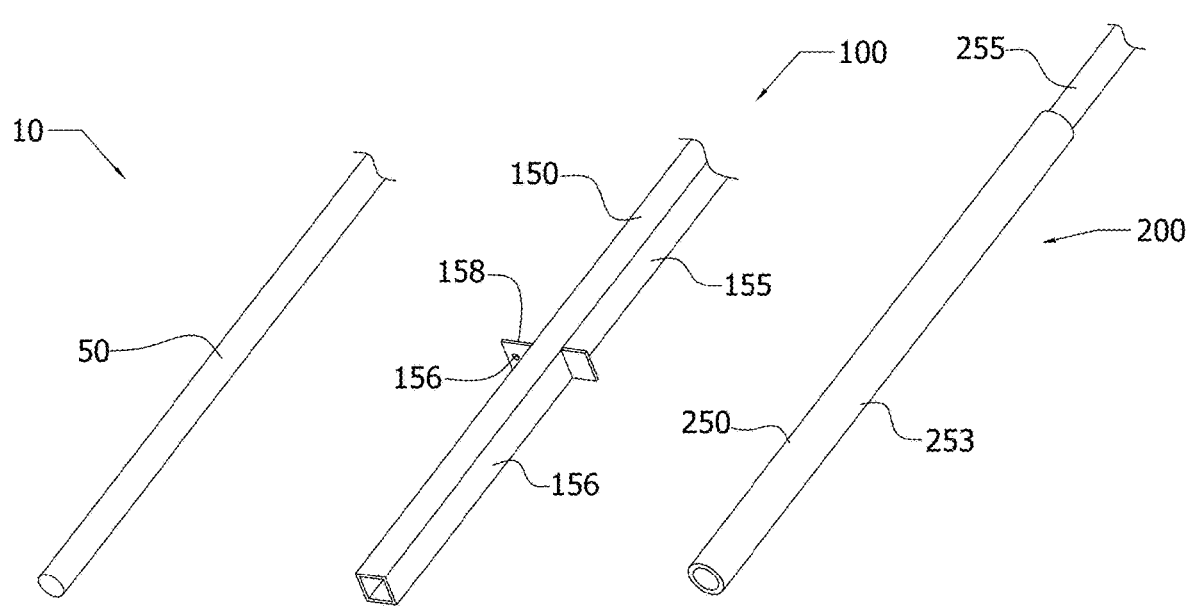
FIG. 4A illustrates by perspective view portions of the exemplary implementation of a poultry treatment apparatus of FIG. 1A.
FIG. 4B illustrates by perspective view portions of another exemplary implementation of a poultry treatment apparatus.
FIG. 4C illustrates by perspective view portions of a third exemplary implementation of a poultry treatment apparatus.
Figure 4D:
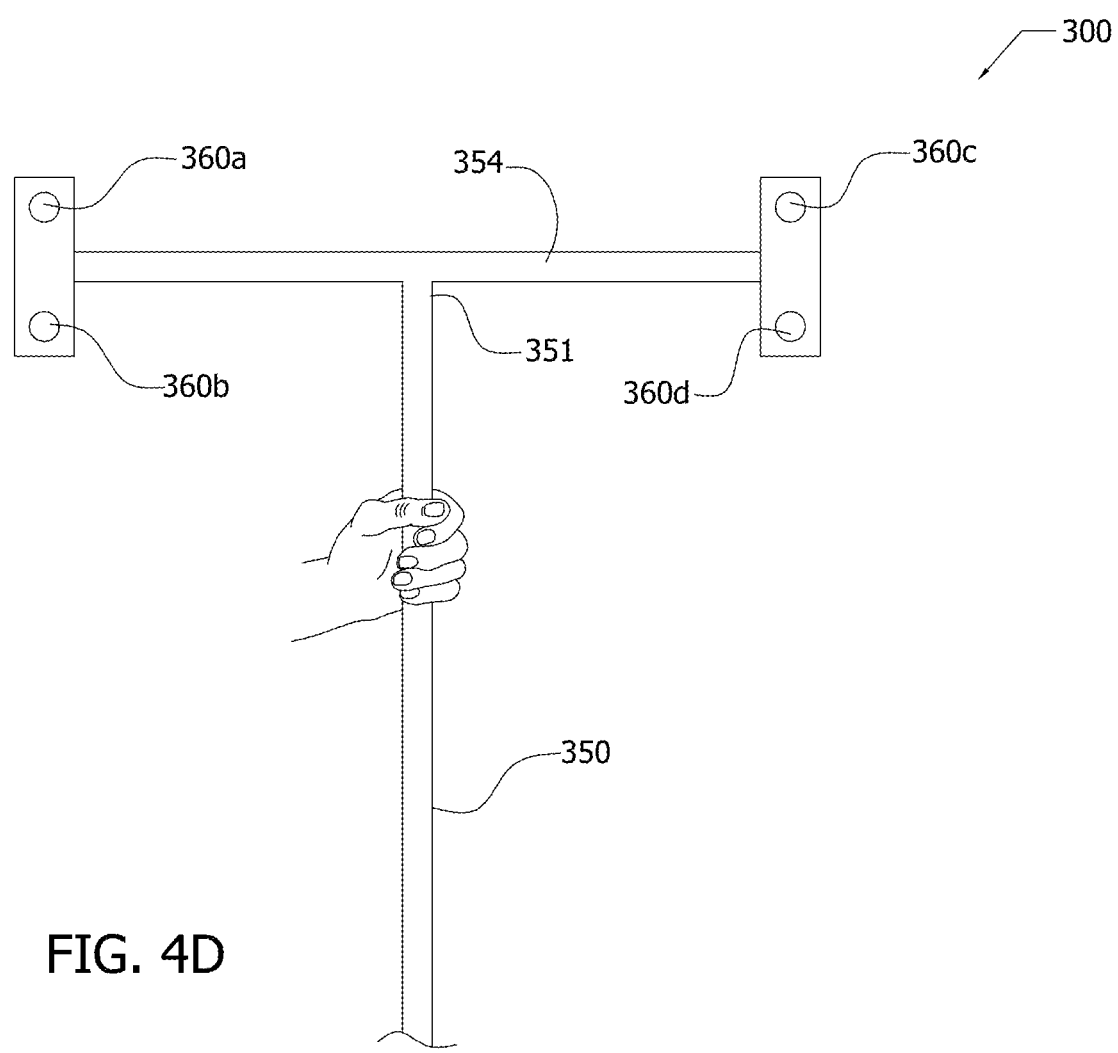
FIG. 4D illustrates by plan view portions of a fourth exemplary implementation of a poultry treatment apparatus.

FIG. 1A illustrates exemplary poultry treatment apparatus 10 including tank 20, pump 30, compressor 40, and boom 50 mounted to cart 12 with one or more nozzles, such as nozzle 60a, 60b, mounted to boom 50. Liquid pathway 34 communicates liquid 14 (see FIG. 1B) from tank 20 to nozzles 60a, 60b, and air pathways 44a, 44b communicate air from compressor 40 to nozzles 60a, 60b, respectively. As illustrated in FIG. 1, cart 12 has four wheels and handle 13 is attached to cart 12 to allow a user to propel the cart 12 manually. In various implementations, cart 12 may have any number of wheels or handles, and cart 12 may include a hitch to allow cart 12 to be towed. Cart 12 may be made of steel, aluminum, wood, various plastics, combinations thereof, and other materials and combinations of materials, as would be readily recognized by those of ordinary skill in the art upon study of this disclosure. Battery 35 communicates electrical power to pump 30 and to compressor 40, in this implementation so that pump 30 and compressor 40 are electrically powered. While exemplary poultry treatment apparatus 10 is illustrated as having two nozzles 60a, 60b for explanatory purposes, it should be recognized that other implementations may have additional nozzles.

As illustrated in FIG. 1B, tank 20 defines reservoir 25 that contains liquid 14 and liquid 14 includes vaccine 15. Reservoir 25 is generally under atmospheric pressure $p_{atm}$ and has a free surface, as illustrated. Tank 20 may be refillable with liquid 14 through port 17 provided for that purpose. Port 17 is sealed by removable cap 18 that protects reservoir 25 including liquid 14 therein from contamination. Tank 20 and cap 18 may be formed of plastic or other materials, as would be readily recognized by those of ordinary skill in the art upon study of this disclosure.

Vaccine 15, as used herein, may include, for example, vaccine(s), antibiotic(s), vitamins, minerals, combinations thereof, or other beneficial materials amenable to being delivered by spray, and vaccine 15 may be solubilized in water as a carrier, in various implementations. The vaccine (s) may, for example, inoculate poultry against New Castle bronchitis, cholera, Marek's disease, or laryngotracheitis. Antibiotics may include, for example, various aminoglycosides, penicillins, lincosamides, or sulfonamides. Vaccine 15, as used herein, may include, for example, live virus vaccines, live bacteria vaccines, killed bacteria vaccine, killed virus vaccines, live protozoa vaccines, and killed protozoa vaccines. In various implementations, vaccine 15, as used herein, may include, for example, disinfectants, prebiotics, probiotics, antibiotics, fungicides, insecticides, competitive exclusion products, anthelmintic, field hygiene products, hatchery hygiene products, litter amendments, rodenticides, supportive care products, vaccine stabilizers, water acidifiers, sanitizer products, vitamin supplements, and other products that may be applied to livestock, poultry, and pets. Exemplary vaccine 15 may include Mycovac-L®, which is live Intervet 6/85 strain of *Mycoplasma gallisepticum* (MG) available from Merck & Co. of Kenilworth N.J. Exemplary vaccine 15 may include Poulvac® EC, which is a modified-live *Escherichia coli* (*E. coli*) vaccine or Poulvac ST, which is a modified-live *Salmonella typhimurium*, both available from Zoetis of Parsippany, N.J. Exemplary vaccine 15 may include sodium chlorite, available, for example, as Pro Oxine from Bio-Cide International Inc, 2650 Venture Drive, Norman, Okla. 73069. Exemplary Pro Oxine is a blend of oxychloro species containing purified sodium chlorite that, when activated, produces chlorine dioxide that may act as a sanitizer and disinfectant for poultry facilities.

The Mycovac-L® has been applied to live poultry using exemplary poultry treatment apparatus 10 with good results that may be due to better coverage, delivery into the air sacs, or both better coverage and delivery into the air sacs.

The Pro Oxine has been applied to a house of 60,000 layers, late first cycle, loosing 60 per day prior to the application of Pro Oxine at the same rate as prescribed for drinking water treatment. With the first application of activated Pro Oxine, the mortality decreased to 30 dead per day the day following the application. With a second application of Pro Oxine, mortality decreased to 15 dead per day. The Pro Oxine may be being delivered into the air sacs of the poultry.

As illustrated in FIG. 1B, reservoir 25 is in fluid communication with pump 30 via liquid pathway 32, and pump 30 communicates fluidly with nozzles 60*a*, 60*b* by fluid pathway 34 to deliver liquid 14 from reservoir 25 to nozzles 60*a*, 60*b*. Liquid pathways 32, 34 may include pipes, tubing, and other fluid conveyances, as well as couplings, connectors, valves, fittings, manifolds, gages, and so forth. Liquid pathways 32, 34 may be formed of rubber or of various plastics, and liquid pathways 32, 34 may be configured to be generally non-reactive to liquid 14, in various implementations. Pump 30, in this implementation, is a positive displacement pump, such as a diaphragm pump manufactured by Pentair/SHURFLO of Costa Mesa, Calif. Pump 30 includes an electric motor powered by battery 35, in this implementation.

As illustrated in FIG. 1B, compressor 40 communicates fluidly with manifold 43 and manifold communicates fluidly with nozzles 60*a*, 60*b* via air pathways 44*a*, 44*b*, respectively, to deliver air 16 under pressure to nozzles 60*a*, 60*b*. In this implementation, compressor 40 draws in air 16 from the ambient environment that is then delivered to nozzles 60*a*, 60*b*. Manifold 43 distributes air from compressor 40 to air pathways 44*a*, 44*b*, in this implementation. Air pathways 42, 44*a*, 44*b*, may include pipes, tubing, and other fluid conveyances, as well as couplings, connectors, valves, fittings, gages, and so forth, and may be formed of various plastics or rubber, in various implementations. Compressor 40 includes an electric motor powered by battery 35, in this implementation. For example, compressor 50 may be a model XD 3000-12 from Oasis Manufacturing of Laguna Hills, Calif.

Battery 35, as illustrated in FIGS. 1A, 1B, is in electrical communication with pump 30 and with compressor 40 to power electrically pump 30 and compressor 40. Various controls may be provided that cooperate with battery 35 in order to control power delivery from battery 35 to pump 30 and compressor 40 as well as to control the operations of pump 30 and compressor 40 including pump speed, compressor speed and the pressures developed by pump 30 and compressor 40. In this implementation, the use of electrical power from battery 35 to power pump 30 and compressor 40 avoids production of noxious exhaust gasses such as carbon monoxide that may be produced by a gasoline engine, as such noxious exhaust gasses may be deleterious to poultry particularly within a structure. Battery 35 may be a lead acid battery and various electrical couplings may be provided about battery 35 to allow recharging of battery 35, for example, from mains electric.

Nozzles 60*a*, 60*b* of poultry treatment apparatus 10 are formed as air atomizing nozzles in exemplary poultry treatment apparatus 10. Liquid 14, which includes vaccine 15, and air 16 are mixed in nozzles 60*a*, 60*b* to produce sprays 62*a*, 62*b*, respectively, as illustrated in FIG. 1B, and sprays 62*a*, 62*b* include atomized droplets 68*a*, 68*b* of liquid 14. Nozzles 60*a*, 60*b*, may be, for example, Quickmist® ¼ QMJ or other Quickmist® series nozzles manufactured by Spraying Systems Co. of Wheaton, Ill. Note that the Quickmist® ¼ QMJ and Quickmist® series nozzles are exemplary only and are not to be considered limiting. Other nozzles may be included in poultry treatment apparatus 10, in other implementations.

As illustrated in FIG. 1B, tiers 70*a*, 70*b* are vertically placed with respect to one another, as illustrated, and poultry may be contained in tiers 70*a*, 70*b*. Nozzles 60*a*, 60*b* are positioned with respect to boom 50 and boom 50 is positioned with respect to cart 12 to direct spray 62*a*, 62*b* into tiers 70*a*, 70*b*, respectively, as illustrated in FIG. 1B. Nozzle 60*a* directs spray 62*a* into tier 70*a*, and nozzle 60*b* directing spray 62*b* into tier 70*b* simultaneously, in this implementation. In other implementations, multiples nozzles, such as nozzle 60*a*, 60*b*, may direct spray into the particular tier, such as one of tier 70*a*, 70*b*. For example, two nozzles may simultaneously direct spray into each tier in which case four nozzles would be mounted to boom 50—two nozzles spraying into tier 70*a* and two nozzles spraying into tier 70*b*. Nozzles 60*a*, 60*b* may be adjustably positionable on boom 30, boom 50 may be adjustably positionable, or both nozzles 60*a*, 60*b* and boom 50 may be adjustably positionable to direct spray 62*a*, 62*b* into tiers 70*a*, 70*b*.

In certain implementations, there may be, multiple tiers. For example, certain implementations may have eight tiers, such as tiers 70*a*, 70*b*, in vertical arrangement, and, thus, for example, eight nozzles, such as nozzles 60*a*, 60*b*, may be mounted to boom 50 with each of the eight nozzles directing spray into one of the eight tiers, respectively, so that spray is directed into each of the eight tiers simultaneously as cart 12 is traversed along the eight tiers. Multiple nozzles may direct spray into each of the eight tiers in this example, so that there may be 16, 32, or some other number of nozzles.

FIG. 2 illustrates the flow of air 16 and liquid 14 in exemplary poultry treatment apparatus 10. As illustrated in FIG. 2, air 16 flows from compressor 40 through air pathway 42 into plenum 45 (see FIG. 2) of manifold 43. Air 16, which is at air pressure $p_g$, is then distributed from plenum 45 into air pathways 44*a*, 44*b* that deliver air 16 to nozzles 60*a*, 60*b*, respectively, generally at air pressure $p_g$. In this implementation, one air pathway, such as air pathway 44*a*, 44*b*, is provided to each nozzle, such as nozzle 60*a*, 60*b*, from manifold 43. As many such air pathways would then be provided from the manifold, such as manifold 43, as there are nozzles—one air pathway per nozzle.

As illustrated in FIG. 2, pump 30 delivers liquid 14 to nozzles 60*a*, 60*b* through liquid pathway 34, and nozzles 60*a*, 60*b* are connected in series along liquid pathway 34. As illustrated in FIG. 2, liquid pathway 34, in this implementation, includes tubes 80, 82 connected to one another by T-connector 81, and T-connector 81 fluidly communicates with nozzle 60*a* to deliver liquid 14 to nozzle 60*a*. Tube 82 is connected to nozzle 60*b* by connector 83 to deliver liquid 14 to nozzle 60*b*. Connector 83 may be, for example, a nipple or an L-connector. Tubes 80, 82 have essentially the same internal diameters 90, 92, respectively, and connectors 81, 83 have essentially the same internal diameters 91, 93, in this implementation. There are no energy dissipators such as orifice plates, valves, and so forth within liquid pathway 34, in this implementation so that the liquid pressure difference between nozzle 60*a* and nozzle 60*b* is generally due to elevation difference z with friction loss in tube 82 and connector 83 being negligible.

In exemplary poultry treatment apparatus 10, pump 30 produces liquid pressure $p_l$ in the liquid pathway 34 proximate pump 30, and compressor 40 produces air pressure $p_g$ in the air pathway 44 proximate compressor 40. Note that pump 30 is separate from compressor 40 so that liquid pressure $p_l$ and air pressure $p_g$ may be set independently of one another. In certain implementations, air pressure $p_g$ may range, for example, from about 30 psi to about 40 psi and liquid pressure $p_l$ may be around 60 psi, so that the liquid pressure $p_l$ is greater than the air pressure $p_g$, in this example. Note that air pressure $p_g$ and liquid pressure $p_l$ may be set independently of one another in exemplary poultry treatment apparatus 10.

As illustrated in FIG. 2, the difference in elevation between nozzle 60*a* and nozzle 60*b* is denoted as z. Assume, for example, that z=20 ft, so that nozzle 60*b* is 20 ft higher in elevation than nozzle 60*a*. Ignoring friction losses through liquid pathway 34 and using a liquid pressure $p_l$ of 60 psi at nozzle 60*a*, the liquid pressure $p_l$ at nozzle 60*b* may then be calculated as approximately 60 psi−((20 ft/33.8 ft)×14.7 psi)=51.3 psi. The ratio of liquid flow rates through nozzles 60*a*, 60*b* may then be calculated as $Q_{60b}/Q_{60a}$=(51.3 psi/60 psi)^½=0.925. Thus, in this example, the variation in liquid flow rate through nozzle 60*b* and nozzle 60*a* is calculated as about 7.5%—i.e. nozzle 60*b* emits about 7.5% less liquid as spray than nozzle 60*a* when z=20 ft.

Exemplary ratios of $Q_{60b}/Q_{60a}$ for various exemplary elevation differences between nozzle 60*a* and nozzle 60*b* corresponding to various exemplary liquid pressures $p_l$ at nozzle 60*a* are given in Table 1 as calculated by the above methodology. Note from Table 1 that the ratio $Q_{60b}/Q_{60a}$ tends toward 1 (equal flow) as the elevation difference between nozzle 60*a* and nozzle 60*b* decreases or as the liquid pressure $p_l$ at nozzle 60*a* is increased. For example, a 10 ft elevation differences (z=10 ft) with liquid pressure 60 psi at nozzle 60*a* is calculated using this methodology to result in about a 3.7% difference in liquid flow rate between nozzles 60*a*, 60*b*. As another example, the difference in liquid flow rate between nozzles 60*a*, 60*b* decreases from about 4.4% to about 3.2% as the liquid pressure $p_l$ at nozzle 60*a* is increased from 50 psi to 70 psi at z=10 ft per Table 1. The 20 ft value as the maximum value of z used in exemplary Table 1 is fairly extreme in practice, so that the height difference between nozzles 60a, 60b may be expected to be less than 20 ft (i.e., z<20 ft) in many practical applications. That is, in many practical applications, the height of the tiers is likely to be less than 20 ft. In various implementations, the elevation difference between tiers may be, for example, about 20 inches to about 30 inches, while the overall elevation difference between the lowest tier and the uppermost tier, for example, may be less than 20 ft.

TABLE 1

| | Calculated $Q_{60b}/Q_{60a}$ | | |
|---|---|---|---|
| z (ft) | 50 psi | 60 psi | 70 psi |
| 5 | 0.978 | 0.982 | 0.984 |
| 10 | 0.956 | 0.963 | 0.968 |
| 15 | 0.933 | 0.944 | 0.952 |
| 20 | 0.909 | 0.925 | 0.936 |

Figure 5:
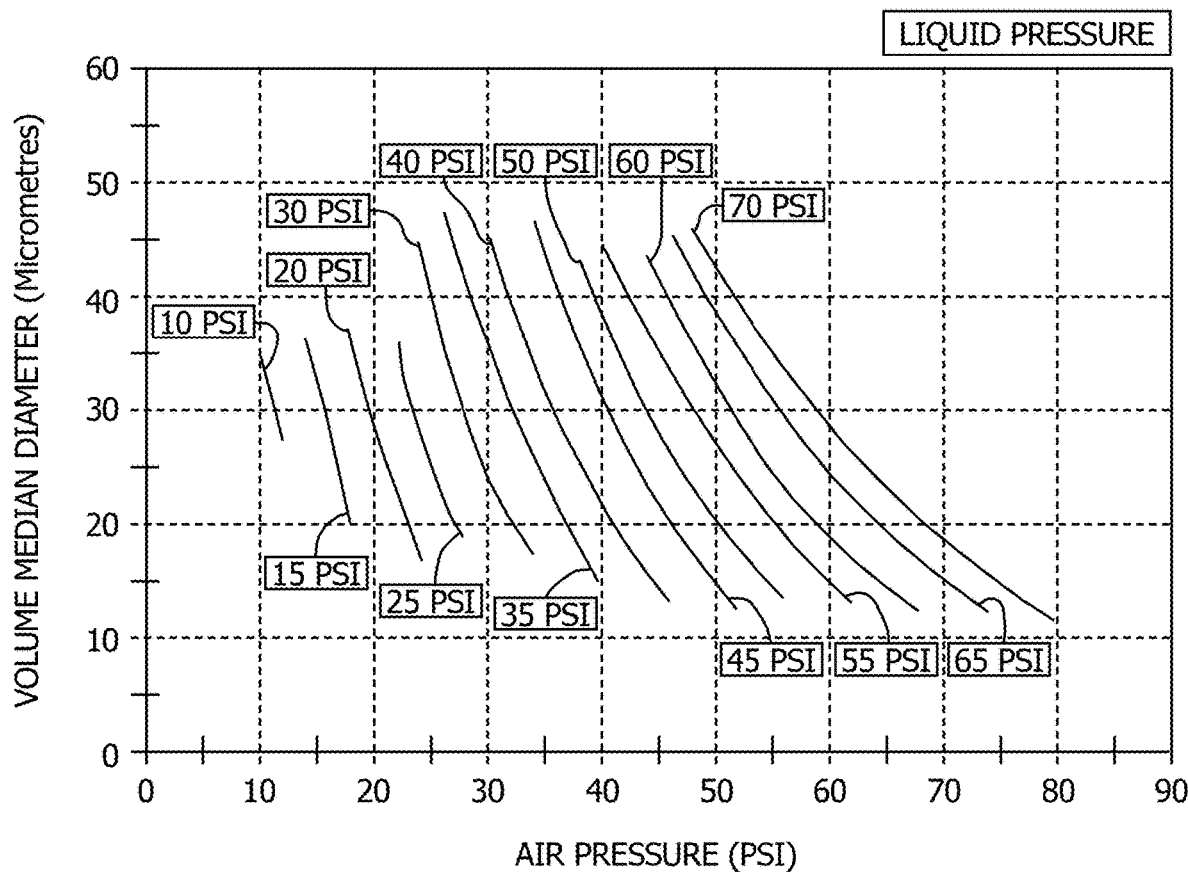
FIG. 5 illustrates by Cartesian plot exemplary experimental relationships between liquid pressure, air pressure, and droplet size for an exemplary Quickmist® ¼ QMJ nozzle as may be included in various implementation of a poultry treatment apparatus according to the present inventions.

Accordingly, it may be concluded from Table 1 that the differences in spray emitted by nozzles 60a, 60b may be acceptable without the need for orifice plates, valves, and so forth within tubes 80, 82 to adjust the quantity of spray 62a, 62b emitted from nozzles 60a, 60b. The ability to increase the liquid pressure $p_l$ independent of air pressure $p_g$ as in exemplary poultry treatment apparatus 10 may allow for control of the liquid flow rate between nozzles 60*a*, 60*b*. By extension, the exemplary theoretical results of Table 1 may be extendable to multiple nozzles, such as nozzles 60*a*, 60*b*, disposed at multiple elevations about boom 50.

FIG. 3 illustrates an exemplary nozzle 60*a*, with other nozzles, such as nozzle 62*b*, of exemplary poultry treatment apparatus 10 being generally similar to nozzle 60*a* of FIG. 3. Liquid 14 and air 16 enter nozzle 60*a* through liquid intake 64*a* and through air intake 66*a*, respectively, as illustrated in FIG. 3, and liquid 14 and air 16 are combined within nozzle 60*a* to emit the liquid 14 from nozzle 60*a* as spray 62*a* including droplets 68*a*.

As illustrated in FIGS. 1A, 1B, boom 50 is mounted to cart 12 and nozzles 60*a*, 60*b* are mounted to boom 50. As illustrated in FIG. 4A, boom 50 of poultry treatment apparatus 10 is formed as a single structural member.

As illustrated in FIG. 4B, boom 150 of poultry treatment apparatus 100 is formed of sections 153, 155 fastened to one another at flanges 156, 158, respectively. Various bolts, nuts, wing nuts, and so forth (not shown) may be utilized to fasten flanges 156, 158 to one another. In such implementations, the length of boom 50 may be adjusted by addition or removal of sections, such as sections 153, 155 to or from boom 150 to position nozzles, such as nozzles 60*a*, 60*b*, to deliver spray, such as spray 62*a*, 62*b*, into tiers, such as tiers 70*a*, 70*b*. Various implementations of boom 150 may include various numbers of sections, such as sections 153, 155.

As illustrated in FIG. 4C, boom 250 of poultry treatment apparatus 200 is formed in sections 253, 255 telescopingly lockably engageable with one another to allow boom 250 to be extended or retracted. Boom 250 may be extended to deliver spray into tiers and boom 250 may be retracted when not in use. Various implementations of boom 250 may include various numbers of sections, such as sections 253, 255.

As illustrated in FIG. 4D, boom 350 of poultry treatment apparatus 300 is detachable from a cart, such as cart 12 of poultry treatment apparatus 10, to allow hand direction of spray from nozzles 360*a*, 360*b*, 360*c*, 360*d* disposed about cross-member 354 that is attached proximate end 351 of boom 350. Any number of nozzles, such as nozzles 360*a*, 360*b*, 360*c*, 360*d*, may be disposed about cross-member 354, in various implementations. Air pathways and liquid pathways (omitted from FIG. 4D for clarity of presentation), such as air pathway 44*a*, 44*b* and liquid pathway 34 of poultry treatment apparatus 10, are provided about boom 350 and cross member 354 that fluidly communicate with nozzles 360*a*, 360*b*, 360*c*, 360*d* and with a compressor and with a tank, such as compressor 40 and tank 20 of poultry treatment apparatus 10, respectively. Boom 350 may be employed to hand direct spray toward free-range poultry that is kept in a larger area, and may be received by a cart, such as cart 12 when not in use.

In various implementations, the boom, such as boom 50, 150, 250, may be positionable with respect to the cart, such as cart 12, for example, to allow positioning of nozzles, such as nozzles 60*a*, 60*b*, and to allow the boom to be placed in a collapsed position about the cart when the boom is not in use. The nozzles may be adjustably mounted to the boom to allow the nozzles to be positioned about the boom. The nozzles may be removably secured to the boom to allow various numbers of nozzles to be mounted to boom in communication with the pump and compressor, such as pump 30 and compressor 40. The boom may be formed, for example, of steel, aluminum, or various plastics. The boom may have various cross-sectional shapes such as circular (see boom 50 illustrated in FIG. 2A) and square (see boom 150 illustrated in FIG. 2B).

In operation of a poultry treatment apparatus, such as poultry treatment apparatus 10, 100, 200, 300 liquid, such as liquid 14, may be placed reservoir, such as reservoir 25, of a tank, such as tank 20. The liquid may include vaccine(s), such as vaccine 15, to be delivered to poultry. The boom, such as boom 50, 150, 250, may be positioned with respect to a cart, such as cart 12, and nozzles, such as nozzles 60*a*, 60*b*, may be mounted about the boom so that the nozzles align with tiers, such as tiers 70*a*, 70*b*, containing poultry. The tiers are arranged vertically, and the nozzles are arranged vertically along the boom in correspondence to the tiers so that at least one nozzle directs spray, such as spray 62*a*, 62*b*, into each tier simultaneously, in various implementations. The pump, such as pump 30, and the compressor, such as compressor 40, are powered ON, and the cart is traversed along the tiers to direct spray into the tiers through the nozzles. The pump and the compressor deliver liquid and air, such as air 16, respectively to the nozzles and the nozzles mix the air with the liquid to produce the spray. The spray may land on poultry, and the poultry may ingest the liquid, for example, while grooming their feathers. The poultry may inhale the spray while the spray is air born. The vaccine(s), antibiotic(s), or other materials may thus be delivered to the poultry by ingestion or inhalation. Alternatively, a boom, such as boom 350 may be manipulated by hand to deliver spray onto poultry in a free-range enclosure.

The droplet size of droplets, such as droplets 68*a*, 68*b*, is illustrated as an exemplary experimentally derived function of air pressure $p_g$ and liquid pressure $p_l$ at the exemplary nozzle (Quickmist® ¼ QMJ) in the Cartesian plot of FIG. 5. According to FIG. 5, the droplet size decreases as the air pressure $p_g$ is increased at a fixed liquid pressure $p_l$. For example, at a liquid pressure $p_l$ of about 55 psi, the droplet size decreases from about 45 μm at an air pressure $p_g$ of about 40 psi to about 14 μm at an air pressure $p_g$ of about 55 psi using FIG. 5. According to FIG. 5, the droplet size increases at a fixed air pressure $p_g$ as the liquid pressure $p_l$ is increased. For example, for an air pressure $p_g$ of about 40 psi, the droplet size increases from about 15 μm to about 50 μm as the liquid pressure $p_l$ is increased from about 35 psi to about 50 psi, according to FIG. 5. Thus, the droplet size may be selected by selection of a combination of liquid pressure $p_l$ and air pressure $p_g$, and the combination of liquid pressure $p_l$ and air pressure $p_g$ may be selected to select a droplet size that, for example, may allow the poultry to inhale the droplets, that may minimize the flow rate of liquid being dispensed, or that may both select the droplet size and the flow rate of liquid being dispensed. The droplet size that optimizes delivery of the vaccine may be vaccine specific. For example, smaller droplet sizes may be more readily inhaled and may penetrate deeper within the airways when inhaled. Smaller droplet sizes may disperse more readily over the tiers for ingestion by the poultry, for example. Larger droplet sizes, for example, may more quickly coat the poultry to then be ingested during grooming, so that larger droplet sizes may have certain advantages over smaller droplet sizes. Various methods may include the step of selecting the droplet size thereby optimizing the delivery of the vaccine by selecting the air pressure at the nozzle and the liquid pressure at the nozzle.

The liquid pressure $p_l$ and air pressure $p_g$, at the nozzle may be selected independent of one another, in various implementations. The liquid pressure $p_l$ and air pressure $p_g$ at the nozzle may be adjusted independently of one another, in various implementations. In some implementations, the liquid pressure $p_l$ may be greater than the air pressure $p_g$ at the nozzle, while, in other implementations, the liquid pressure $p_l$ may be less than the air pressure $p_g$ at the nozzle. In still other implementations, the liquid pressure $p_l$ may be about equal to the air pressure $p_g$ at the nozzle.

Figure 6B:
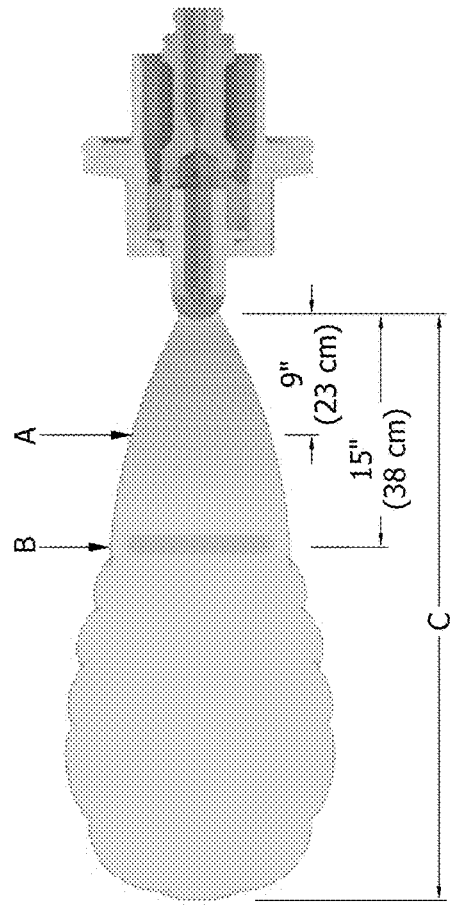
FIG. 6A illustrates by chart exemplary experimental relationships between liquid pressure, air pressure, liquid flow rate, and air flow rate for various exemplary Quickmist® ¼ QMJ nozzles as may be included in various implementations of a poultry treatment apparatus according to the present inventions; and, FIG. 6B illustrates by chart exemplary experimental relationships between liquid pressure, air pressure, liquid flow rate, and air flow rate for various exemplary Quickmist® ¼ QMJ nozzles as may be included in various implementations of a poultry treatment apparatus according to the present inventions.

FIGS. 6A and 6B illustrate by chart the air flow rate, liquid flow rate, air pressure, and liquid pressure relationships for exemplary nozzle (Quickmist® ¼ QMJ), as may be included in various implementation of a poultry treatment apparatus according to the present inventions. As per FIGS. 6A and 6B, the liquid pressure $p_l$ and the air pressure $p_g$ at the nozzle may be selected to select the liquid flow rate and the air flow rate.

The foregoing discussion along with the Figures discloses and describes various exemplary implementations. These implementations are not meant to limit the scope of coverage, but, instead, to assist in understanding the context of the language used in this specification and in the claims. The Abstract is presented to meet requirements of 37 C.F.R. § 1.72(b) only. The Abstract is not intended to identify key elements of the apparatus and methods disclosed herein or to delineate the scope thereof. Upon study of this disclosure and the exemplary implementations herein, one of ordinary skill in the art may readily recognize that various changes, modifications and variations can be made thereto without departing from the spirit and scope of the inventions as defined in the following claims.

The invention claimed is:

1. A poultry treatment apparatus, comprising:
a tank containing a liquid comprising a vaccine an air pathway in fluid communication with a compressor, a first nozzle, and a second nozzle to communicate a compressed air from the compressor to the first nozzle and to the second nozzle;
a liquid pathway in fluid communication with a pump, the first nozzle, and the second nozzle to communicate the liquid from the pump to the first nozzle and to the second nozzle, the liquid in combination with the compressed air emanates as a first spray from the first nozzle and as a second spray from the second nozzle, the liquid pathway is separated from the air pathway exclusive of the first nozzle and exclusive of the second nozzle;
a boom, the first nozzle secured to the boom at a first elevation to deliver the first spray into a first tier, the second nozzle secured to the boom at a second elevation to deliver the second spray into a second tier, the second tier being at a different elevation than the first tier; and
wherein the tank, the compressor, the pump, and the boom are attached to a cart traversable along the first tier and the second tier wherein a liquid pressure $p_l$ of the liquid at the first nozzle is greater than an air pressure $p_g$ of the compressed air, the first nozzle being elevated above a liquid surface of the liquid within the tank.

2. The apparatus of claim 1, the liquid pressure between about 30 psi and about 60 psi proximate a discharge side of the pump and the air pressure $p_g$ is within a range of from about 30 psi to about 40 psi.

3. The apparatus of claim 1, a flow rate difference of the liquid between the first nozzle and the second nozzle being less than about 10%.

4. The apparatus of claim 1, a flow rate difference of the liquid between the first nozzle and the second nozzle being less than about 5%.

5. The apparatus of claim 1, the first nozzle and the second nozzle fluidly connected in series with the pump.

6. The apparatus of claim 1, a pressure difference in the liquid pressure $p_l$ of the liquid between the first nozzle and the second nozzle is generally proportional to an elevation difference between the first nozzle and the second nozzle.

7. The apparatus of claim 1, a battery disposed on the cart in electrical communication with the pump and with the compressor to power the pump and the compressor.

8. The apparatus of claim 1, the vaccine selected from a group consisting of live virus vaccine, live bacteria vaccine, killed bacteria vaccine, killed virus vaccine, live protozoa vaccine, and killed protozoa vaccine.

9. The apparatus of claim 1, the vaccine comprises sodium chlorite.

10. The apparatus of claim 1, the boom is detachable from the cart to allow a user to direct the delivery of the spray by hand orientation of the boom.

11. The apparatus of claim 1, the first spray having a droplet size between about 15 μm and about 45 μm.

* * * * *